US005785823A

United States Patent [19]

Meurer et al.

[11] Patent Number: 5,785,823
[45] Date of Patent: Jul. 28, 1998

[54] PROCESS FOR THE PURIFICATION OF BISPHENOL

[75] Inventors: Kurt-Peter Meurer, Leverkusen, Germany; Tony Van Osselaer, Belsele, Belgium; Werner Verhoeven, Heide-Kalmthout, Belgium; Johan Vaes, Kalmthout, Belgium; Ignace Hooftman, Kruibeke, Belgium; Willy Van Herck, Brasschaat, Belgium; Claus Wulff; Jürgen Hinz, both of Krefeld, Germany; Alfred Eitel, Dormagen, Germany; Kaspar Hallenberger, Leverkusen, Germany

[73] Assignee: Bayer AG Konzernverwaltung RP, Germany

[21] Appl. No.: 691,402

[22] Filed: Aug. 2, 1996

[30] Foreign Application Priority Data

Aug. 14, 1995 [DE] Germany ............... 195 29 855.1

[51] Int. Cl.$^6$ ............... B01D 3/00; C07C 37/74
[52] U.S. Cl. ............... 203/71; 203/14; 203/73; 203/80; 568/724
[58] Field of Search ............... 203/29, 38, 14, 203/18, 71, 73, 77, 80; 568/724

[56] References Cited

U.S. PATENT DOCUMENTS

| | | | |
|---|---|---|---|
| 4,158,611 | 6/1979 | Cooke | 203/80 |
| 4,387,251 | 6/1983 | Meyer et al. | 568/727 |
| 4,400,553 | 8/1983 | Aneja | 568/724 |
| 4,400,555 | 8/1983 | Mendiratta | 568/728 |
| 5,269,887 | 12/1993 | Jakob et al. | 203/91 |

FOREIGN PATENT DOCUMENTS

| | | |
|---|---|---|
| 678415 | 9/1966 | Belgium . |
| 0 552 518 | 7/1993 | European Pat. Off. . |
| 0 679 626 | 11/1995 | European Pat. Off. . |
| 29 18 990 | 11/1980 | Germany . |

*Primary Examiner*—Virginia Manoharan
*Attorney, Agent, or Firm*—Connolly & Hutz

[57] ABSTRACT

A process for preparing bisphenol A which has a purity of at least 99.95 wt. % of p,p-bisphenol A (BPA). Thermally stable and colour-stable BPA purified in accordance with the invention produces improved thermal and colour stability and improved optical transparency in polymers such as e.g. polycarbonates prepared therefrom.

2 Claims, No Drawings

PROCESS FOR THE PURIFICATION OF BISPHENOL

The invention relates to a process for preparing bisphenol A which has a purity of at least 99.95 wt. % of p,p-bisphenol A (BPA). Thermally stable and colour-stable BPA, purified according to the invention, produces improved thermal and colour stability and an improved optical transparency in polymers prepared therefrom, such as for instance a polycarbonate.

p,p-bisphenol A (BPA) is prepared for example by known processes from acetone and phenol in the presence of optionally modified ion-exchange resins (e.g. DE-A-3 727 641, corresponding to U.S. Pat. No. 912,263).

Production of extremely pure bisphenol A is known. DE-A-4 213 872 describes how bisphenol A can be produced with a degree of purity of 99.91 wt. %. Purification is performed by crystallising a BPA/phenol adduct then filtering the adduct and desorbing the phenol.

D-EA-44 13 396 describes how high purity bisphenol A can be obtained by distilling a melt which contains at least 90 wt. % of BPA in two stages and separating the barely/readily volatile and involatile components. A stream of nitrogen is used to remove phenol from the melt used and to render the melt inert. Preliminary purification of the BPA melt is achieved by means of crystallisation, filtration and desorption.

It has now been found that the purification steps for a phenolic BPA solution which are used on a large scale such as crystallisation, filtration and desorption of the BPA/phenol adduct can be eliminated if the phenolic solution containing p,p-bisphenol, such as is produced during the preparation of BPA from phenol and acetone, is purified by a sequence of distillation stages connected in series.

The invention therefore provides a process for obtaining bisphenol A with a degree of purity greater than 99.95 wt. % and a Hazen (APHA) colour index of <5 from the reaction solution which is obtained during the production of BPA from acetone and phenol in the presence of sulphonic acid ion-exchangers optionally modified with mercapto-amines and/or thiazolidines and/or thiocarboxylic acids, wherein
a) the phenolic solution is adjusted to a concentration of 10 to 40 wt. % of p,p-BPA at a temperature of 60°–80° C.,
b) the solution prepared in this way is then supplied to a sequence of columns connected in series, wherein
c) in a first distillation step, the water and residual acetone, optionally phenol, are removed from the reaction solution being discharged from the reactor, then
d) in a second distillation step, the anhydrous solution prepared in this way is adjusted to a concentration of 70 to 97 wt. % of p,p-BPA at the base of the column, then
e) in a third distillation step, barely volatile and involatile components are removed from the solution obtained in this way, then
f) in a fourth distillation step, the readily volatile components and residual phenol distilled over with the p,p-BPA are removed, then
g) the p,p-BPA melt obtained from the base of the column is worked up in a conventional manner.

The p,p-bisphenol A prepared in this way is used as the raw material for polymers such as polycarbonates or epoxy resins.

The fact that the phenolic BPA solution can be purified simply by a sequence of distillation steps arranged in series could not have been predicted because, as is known, BPA and the isomers contained therein isomerise at very high temperatures and this results in a very poor colour index for the BPA melt and the BPA solid product.

The distillation process for a phenolic BPA solution also has the advantage that complicated multi-stage crystallisation processes, the use of rotating filters and centrifuges and the use of desorption units which are prone to break down are not required. Technically complicated maintenance-intensive operation of process equipment is therefore avoided and the availability of the plant is increased.

EXAMPLES

Example 1

Preparing a reaction solution 8 l of phenol-moist sulphonated polystyrene resin (Lewatit SC 102, Bayer AG) are initially introduced above glass wool packing in a double-walled glass reactor (10 l) which is maintained at 80° C. This is continuously rendered inert by means of nitrogen. Then a solution (1 l/h) of 95.5% phenol and 4.5% acetone which has been preheated to 70° C. is fed continuously into the reactor from above.

A phenolic solution with the following composition is obtained at the lower discharge point from the reactor: phenol 84%; acetone 1%; water 1.2%; p,p-BPA 11.6%; o,p-BPA 1.6%; DMX 24 ppm; chromane 3700 ppm; indane 42 ppm; trisphenol 1780 ppm; mol. wt. 402, 410 ppm; remainder 110 ppm.

Example 2

Distilling acetone/water from the reaction solution 10 l of a phenolic solution with the above composition (discharged from the reactor) are initially placed in a 3-necked flask and distilled, under inert conditions, over two plate columns with 10 separating stages. Distillation is performed at 150 mbar, the temperature at the base of the column is 126° C.

A distillate with the following composition is obtained: acetone 37.5%; water 58.5%; phenol 4%; mesitylene 25 ppm; anisole 10ppm; methanol 300 ppm.

The product at the base of the column had the following composition: phenol 85.9 %; p,p-BPA 11.9%; o,p-BPA 1.6%; DMX 25 ppm; chromane 3765 ppm; indane 43 ppm; trisphenol 1820 ppm; mol. wt. 402, 420 ppm; remainder 102 ppm.

Example 3

Distilling phenol out of the anhydrous solution

Phenol distillation is performed at 100 mbar, the temperature at the head of the column is 120° C. The distillate contains 99.95% phenol and 50 ppm o-cresol. The product at the base of the column contains: 4400 ppm phenol; 83.7% p,p-BPA; 11.4% o,p-BPA; 173 ppm DMX; 2.7% chromane; 303 ppm indane; 1.3% trisphenol; 3000 ppm of mol. wt. 402 and 700 ppm of residual isomers.

Example 4

Removing barely volatile and readily volatile components

The above solution is distilled at 2 mbar with a base temperature of 226° C. First, barely volatile components are enriched at the base of the column and eliminated.

The readily volatile components and BPA distil over at the head and are taken to a second column. There, the readily volatile components and residual phenol are isolated via the head at 2 mbar. The base product contains extremely pure p,p-BPA (>99.95 wt. %).

This distillation is performed, for instance, in accordance with a known process for the distillation of BPA melts which is described in DE-A-44 13 396. A bisphenol A is obtained (in 98% yield) with a purity of 99.98 wt. % p,p-BPA.

From a mass balance, less than 2% of p,p-BPA is lost.

We claim:

1. A process for obtaining bisphenol A with a degree of purity greater than 99.95 wt. % and a Hazen (APHA) colour index of <5 from a reaction solution which is obtained in a reactor during the production of bisphenol A from acetone and phenol in the presence of sulphonic acid ion-exchangers optionally modified with mercapto-amines and/or thiazolidines and/or thiocarboxylic acids, which comprises:
   a) adjusting the reaction solution to a concentration of 10 to 40 wt. % of p,p-bisphenol A(BPA) at a temperature of 60°–80° C.,
   b) supplying the resulting solution to a sequence of columns connected in series, further comprising
   c) removing, in a first distillation step, water and residual acetone and, optionally phenol, from the reaction solution being discharged from the reactor,
   d) adjusting, in a second distillation step, a resulting anhydrous solution to a concentration of 70 to 97 wt. % of p,p-BPA at the base of the column,
   e) removing, in a third distillations step, barely volatile and involatile components from the resulting solution,
   f) removing, in a fourth distillation step, readily volatile components and residual phenol distilled over with the p,p-BPA to leave a p,p-BPA melt at the base of a fourth distillation column, and
   g) recovering p,p-BPA from the p,p-BPA melt at the base of the fourth distillation column.

2. A process for obtaining bisphenol A as claimed in claim 1 wherein polycarbonates and epoxy resins are prepared from the p,p-BPA recovered in step (g).

* * * * *